United States Patent [19]

Solomons et al.

[11] 3,968,163

[45] July 6, 1976

[54] PREPARATION OF 4 AND 5-METHYLINDANES

[75] Inventors: William Ebenezer Solomons; Ian William Mathison, both of Memphis, Tenn.

[73] Assignee: Marion Laboratories, Inc., Kansas City, Mo.

[22] Filed: Aug. 19, 1974

[21] Appl. No.: 498,558

[52] U.S. Cl. ............................ 260/599; 260/566 R; 260/668 R
[51] Int. Cl.$^2$ .......................................... C07C 47/52
[58] Field of Search .................................... 260/599

[56] References Cited
OTHER PUBLICATIONS

Wagner, et al., Synthetic Organic Chem., John Wiley & Sons Inc., pp. 284–285 & 728–729 (1965).

Olah, Friedel Crafts & Related Reactions, Interscience Publishers, pp. 118–119 (1963).

*Primary Examiner*—James O. Thomas, Jr.
*Assistant Examiner*—G. Breitenstein
*Attorney, Agent, or Firm*—Merriam, Marshall, Shapiro & Klose

[57] ABSTRACT

Indane is reacted with an $\alpha,\alpha$-dichloromethyl lower alkyl ether, the reaction mixture is treated with water to produce a mixture of 4-formylindane and 5-formylindane, the aldehyde isomers are separated and the aldehydes are catalytically hydrogenated to produce 4-methylindane and 5-methylindane.

1 Claim, No Drawings

PREPARATION OF 4 AND 5-METHYLINDANES

This invention relates to the production of 4-formylindane and 5-formylindane, and the 4-methylindane and 5-methylindane derivatives of the said aldehydes.

Brit. Pat. No. 1,133,457 discloses 4-formylindane and 5-formylindane as useful starting materials in the production of various aminoalkyl indanes which produce vasodilation and improve peripheral blood circulation. R. T. Arnold in *J. Am. Chem. Soc.*, 61, 1405 (1939) also discloses 5-formylindane.

Arnold, supra, discloses the reaction of indane with formaldehyde, hydrochloric acid and sulfuric acid to produce 5-chloromethylindane which on treatment with hexamethylenetetramine in aqueous ethanol yields 5-formylindane. Plattner and Roniger in *Helv. Chim. Acta*, 25, 590 (1942) utilize 5-chloromethylindane (prepared by Arnold's procedure) to produce 5-methylindane by catalytic hydrogenation. Plattner and Roniger use the 5-methylindane as a starting material to produce 5-methyl azulenes. Azulenes have antiinflammatory properties. See *Merck Index*, 8th Ed., page 115. They are also useful coloring agents.

Hinkel el al. in *J. Chem. Soc.*, 339 (1936) disclose the reaction of indane (also called dihydroindene and hydrindene) with hydrogen cyanide in tetrachloroethane in the presence of aluminum chloride followed by decomposition of the reaction mixture to yield 5-formylindane and probably also some 4-formylindane. The 5-formylindane was characterized by means of its aniline derivative.

5-Methylindane is a commercial compound obtained from petroleum distillates. It is available in limited amounts at relatively high cost.

Because of the interest in 4 or 5-formylindanes and 4 or 5-methylindanes it is desirable that alternative processes be available for producing these compounds in both experimental and commercial quantities.

According to the present invention there is provided a novel process of producing 4 or 5-formylindanes and 4 and 5-methylindanes using indane as the starting material. In the invention, indane is first formylated using a Friedel-Crafts catalyst and α,α-dichloromethyl lower alkyl ether followed by water to give 5-formylindane together with 4-formylindane. The aldehydes are separated by forming their anilides followed by hydrolysis of the anilides to give the free separate 4-formylindane and 5-formylindane. Catalytic hydrogenation then is used to convert the aldehydes to 4-methylindane and 5-methylindane. This overall process can be represented as follows:

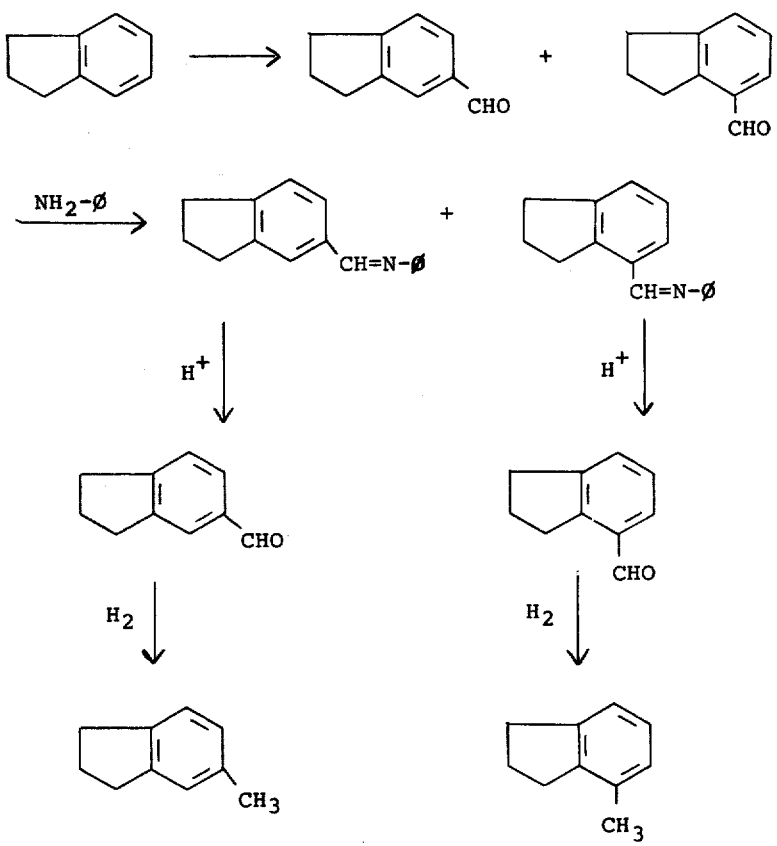

wherein φ is phenyl.

In the first step of the process, indane is formylated according to the method of Alfred Rieche et al. in *Chem. Ber.*, 93, 88 (1960) using a Friedel-Crafts catalyst such as stannic tetrachloride, aluminum trichloride or titanium tetrachloride and an α,α-dichloromethyl lower alkyl ether, such as α,α-dichloromethyl methyl ether and α,α-dichloromethyl n-butyl ether, followed by water. The reaction is effected first under anhydrous conditions in a suitable liquid reaction medium, such as dichloromethane, followed by water. The reaction gives a mixture of 4-formylindane and 5-formylindane. The presence of a mixture of isomeric aldehydes is shown by gas chromatography. A mixture of 4-formylindane and 5-formylindane formed by the described procedure contains about 80% of the 5-formyl and 20% of the 4-formyl isomers.

By treating the mixture of aldehydes with aniline there is obtained a mixture of anilides which are readily separated by fractional crystallization or column chromatography. For example, the anilide of 5-formylindane readily crystallizes from acetonitrile while the anilide of 4-formylindane remains dissolved in that solvent. After the anilide of 5-formylindane is recovered by preferential crystallization, the anilide of 4-formylindane can be isolated by removing the solvent under reduced pressure with heating.

Each of the anilides of 4-formylindane and 5-formylindane upon hydrolysis with an acid, such as hydrochloric acid, yields the free and separated 4-formylindane and 5-formylindane.

Reduction of the 4-formylindane and 5-formylindane to the appropriate 4-methylindane and 5-methylindane is readily effected catalytically using hydrogen and a suitable catalyst such as palladium. The hydrogenation is effected by placing the appropriate aldehyde in glacial acetic acid containing the catalyst and a small amount of concentrated hydrochloric acid. The hydrogenation proceeds readily at room temperature using a hydrogen pressure of about 25 to 100 psig. After hydrogen uptake has ceased the product can be recovered from the reaction mixture by conventional methods.

The following examples are presented to illustrate the invention.

EXAMPLE 1

4-Formylindane, 5-Formylindane and Anilides Thereof

A solution of indane (50 g, 0.423 mole) and 300 ml of $CH_2Cl_2$ was cooled to 0°C. in an ice salt bath before 106.5 g (0.562 mole) of titanium tetrachloride was poured in. After additional cooling, 64.35 g (0.560 mole) of α,α-dichloromethyl methyl ether was added rapidly dropwise allowing the evolution of HCl gas to subside before removing the ice bath and stirring for 30 minutes. The mixture was poured over 600-700 ml of ice and water, well shaken and then washed with water, 200 ml of 10% $Na_2CO_3$ solution, and finally with water. Often ether was added to invert the phases before washing. The solvent was evaporated and the residual dark oil was distilled under high vacuum giving a major fraction, 38.42 g (84%), b.p. 132°–133°C. (15–16 mm). Gas chromatography showed the presence of two components with similar retention times in a ratio of about 20:80. The compounds were 4-formylindane and 5-formylindane with the 5-aldehyde being present in greatest quantity and having the longest retention time.

In a 250 ml round-bottom flask 22.41 g (0.15 mole) of a mixture of 4-formylindane and 5-formylindane, 12.42 g (0.13 mole) of aniline and 125 ml of dry benzene was refluxed for 18 hours under a Dean-Stark trap and condenser. Water was removed twice from the Dean-Stark trap during te first 4 to 6 hours of refluxing. The solvent was thoroughly removed on a rotary evaporator and the remaining oil solidified on cooling. The solid was dissolved in hot acetonitrile and upon cooling the anilide of 5-formylindane crystallized out, m.p. 85°–86°C. It was refluxed in 10% hydrochloric acid, the acid solution was extracted with ether and the ether was evaporated to give 5-formylindane as a slightly orange oil (13,77 g).

The anilide of 4-formylindane is isolated from the acetonitrile mother liquor from which the 5-isomer was removed, by removing the solvent under reduced pressure with heating. Hydrolysis of the anilide, in the manner described above for the 5-isomer, gives 4-formylindane.

EXAMPLE 2

4-Methylindane and 5-Methylindane

Low pressure (45 psi) hydrogenation of 16.78 g (0.115 mole) of 5-formylindane over 2.5 g of 5% Pd/C in 30 ml of glacial acetic acid and 25 drops of conc. HCl yielded 5-methylindane. After adding a filter aid to the reaction mixture and filtering, the filtrate was made basic with 40 g (1 mole) sodium hydroxide in 300 ml of water at 0°C. This was extracted with 3 × 90 ml of ether, the ether solution was washed with water, dried over sodium sulfate and concentrated. The concentrated liquid was distilled at atmospheric pressure, b.p. 197°–198°C. yielding 12.70 g. (84%) of clear liquid.

By catalytically hydrogenating 4-formylindane in the described manner there is obtained 4-methylindane.

The foregoing detailed description has been given for clearness of understanding only, and no unnecessary limitations should be understood therefrom, as modifications will be obvious to those skilled in the art.

What is claimed is:

1. The process which comprises reacting indane with α,α-dichloromethyl methyl ether in the presence of titanium tetrachloride under anhydrous conditions and decomposing the resulting reaction mixture with water to form a mixture of 4-formylindane and 5-formylindane,
combining the mixture of 4-formylindane and 5-formylindane with aniline to form a mixture of the anilide of 4-formylindane and the anilide of 5-formylindane,
adding the mixture of the anilide of 4-formylindane and the anilide of 5-formylindane to acetonitrile in which the anilide of 5-formylindane preferentially crystallizes while the anilide of 4-formylindane remains dissolved in the acetonitrile,
hydrolyzing the separated anilide of 5-formylindane to give separated free 5-formylindane, and
hydrolyzing the separated anilide of 4-formylindane to give separated free 4-formylindane.

* * * * *